United States Patent
Brophy

(10) Patent No.: US 11,141,558 B2
(45) Date of Patent: Oct. 12, 2021

(54) MENTAL TARGETING SYSTEM

(71) Applicant: Steve Brophy, Plymouth, MI (US)

(72) Inventor: Steve Brophy, Plymouth, MI (US)

( * ) Notice: Subject to any disclaimer, the term of this patent is extended or adjusted under 35 U.S.C. 154(b) by 266 days.

(21) Appl. No.: 16/405,059

(22) Filed: May 7, 2019

(65) Prior Publication Data

US 2020/0230345 A1 Jul. 23, 2020

Related U.S. Application Data

(60) Provisional application No. 62/793,954, filed on Jan. 18, 2019.

(51) Int. Cl.
| | |
|---|---|
| *A61M 21/02* | (2006.01) |
| *A61M 21/00* | (2006.01) |
| *G10L 25/84* | (2013.01) |
| *H04R 25/00* | (2006.01) |

(52) U.S. Cl.
CPC ..... *A61M 21/02* (2013.01); *A61M 2021/0027* (2013.01); *A61M 2210/0662* (2013.01); *G10H 2250/371* (2013.01); *G10L 25/84* (2013.01); *H04R 25/75* (2013.01)

(58) Field of Classification Search
CPC ............. A61M 21/00–02; G04G 13/00–028
See application file for complete search history.

(56) References Cited

U.S. PATENT DOCUMENTS

| | | | |
|---|---|---|---|
| 8,328,368 B2 | 12/2012 | Luciano | |
| 8,593,912 B1* | 11/2013 | Amores | G04G 11/00 368/79 |
| 9,479,853 B1 | 10/2016 | Marquette et al. | |
| 9,694,154 B2 | 7/2017 | Genereux et al. | |
| 2003/0198137 A1* | 10/2003 | Gorden | G04G 13/028 368/12 |
| 2007/0211575 A1* | 9/2007 | Rosen | G04G 13/026 368/10 |
| 2007/0242225 A1 | 10/2007 | Bragg et al. | |
| 2008/0143966 A1 | 6/2008 | Mastrosimone-Gese et al. | |
| 2009/0208030 A1 | 8/2009 | Anderson et al. | |
| 2013/0037461 A1* | 2/2013 | Biewer | A61M 1/28 210/85 |
| 2015/0177704 A1* | 6/2015 | Howell | G04G 13/02 368/10 |
| 2015/0276178 A1* | 10/2015 | Chien | F21V 23/0442 362/95 |

(Continued)

*Primary Examiner* — Thaddeus B Cox
(74) *Attorney, Agent, or Firm* — Boudwin Intellectual Property; Daniel Boudwin

(57) ABSTRACT

A mental targeting system. The mental targeting system has a housing which includes a base, at least one sidewall extending from the base, and a top surface, all of which defines an interior volume. A control circuit is disposed in the interior volume which is in electrical communication with a speaker, a microphone, a projector, a plurality of buttons, and a non-transitory computer readable medium. The speaker is disposed in a sidewall and plays sounds stored in the non-transitory computer readable medium. The projector includes a projection lens, and is disposed on the top of the housing where it projects light through a removably securable disc. A slot disposed in the sidewall below the projection lens is used to deposit and retrieve the disc. Full insertion of the disc into the slot positions a portion of the disc directly below, and parallel with, the projection lens.

16 Claims, 4 Drawing Sheets

(56) References Cited

U.S. PATENT DOCUMENTS

2017/0285576 A1* 10/2017 Habash ................ G04G 13/02
2018/0129129 A1*  5/2018 Seger ..................... G03B 21/32
2018/0159967 A1*  6/2018 Rebot .................... G03B 29/00

\* cited by examiner

MENTAL TARGETING SYSTEM

CROSS REFERENCE TO RELATED APPLICATIONS

This application claims the benefit of U.S. Provisional Application No. 62/793,954 filed on Jan. 18, 2019. The above identified patent application is herein incorporated by reference in its entirety to provide continuity of disclosure.

BACKGROUND OF THE INVENTION

The present invention relates to learning devices, specifically in the realm of mental targeting. More particularly, the present invention provides for a device that projects images on a disc and plays audio stored on a non-transitory computer readable medium thereby enabling an individual to utilize visual and mental targeting to set goals and work towards achieving them.

Many people lead busy and complicated lives and are unable to organize themselves and generate or focus on a series of tasks to accomplish important goals in their lives. Some people feel inundated with information and noise assailing them at all times of the day, causing them to get distracted from important tasks and goals. This inability to focus can lead such people to experience anxiety and a lack of motivation to get through their day. Such demotivated people may fail to create, recognize, and pursue worthwhile goals in life which leads to under-achievement and mediocrity, as well as negative responses and perceptions in others as mediocrity and under-achievement are closely associated with people who lack goals altogether. Positive thinking and focusing on goals are important for personal growth in individuals of all ages.

One way to counter-act the chaos of daily life is with a device that guides an individual in an end-of-day mental centering activity that creates positive habits and reinforces goal formation through visual and mental targeting of the goals right before the individual falls asleep. Such activities allow the reticular activation center within the brain to work on the next steps to bring the goal into being while the individual sleeps. This process creates further clarity and a positive feedback loop wherein the individual starts their day with a fresh mind and allows the individual to think clearly about how to approach their goals, and what the next step is to achieve those goals. Positive identification, pursuit, and focusing on worthwhile personalized goals is essential for individuals to realize a larger percentage of their life's potential. The process of identification, pursuit, focusing on goals, and reinforcement is the fundamental recipe for achievement at all ages. The present device supports those who have goals but lack the ability to overcome the noise of daily life, and to focus on and meaningfully pursue and make progress towards their personal goals.

Devices have been disclosed in the known art that relate to learning and goal pursuit. These include devices that have been patented and disclosed in patent application publications. However, the devices in the known art have several drawbacks. Some such devices do not provide the user with the ability to personalize their goals and learning experiences by utilization of stimuli such as sounds including both generic voices and the user's own voice. Other devices fail to allow the user to customize the stimuli to focus on the user's unique and particular goals. Still other such devices lack a timer which allows a user to allocate a pre-determined amount of time on introspection and contemplation of the stimuli.

The present invention substantially diverges in design elements from the known art and consequently it is clear that there is a need in the art for an improvement to existing learning devices, specifically in the realm of mental targeting. In this regard, the present invention substantially fulfills these needs.

SUMMARY OF THE INVENTION

In view of the foregoing disadvantages inherent in the known types of learning devices now present in the prior art, the present invention provides a mental targeting system wherein the same can be utilized to aid a user in defining, contemplating, and achieving goals. The present mental targeting system comprises a housing which includes a base, at least one sidewall extending from the base, and a top surface, all of which defines an interior volume. A control circuit is disposed in the interior volume which is in electrical communication with a speaker, a microphone, a projector, a plurality of buttons, and a non-transitory computer readable medium. The speaker is disposed in a sidewall and plays sounds stored in the non-transitory computer readable medium. The projector includes a projection lens, and is disposed on the top of the housing where it projects illumination through a removably securable disc. A slot in the sidewall, in a position below the projection lens, is used to deposit and retrieve the disc. Full insertion of the disc into the slot positions a portion of the disc directly below, and parallel with, the projection lens.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
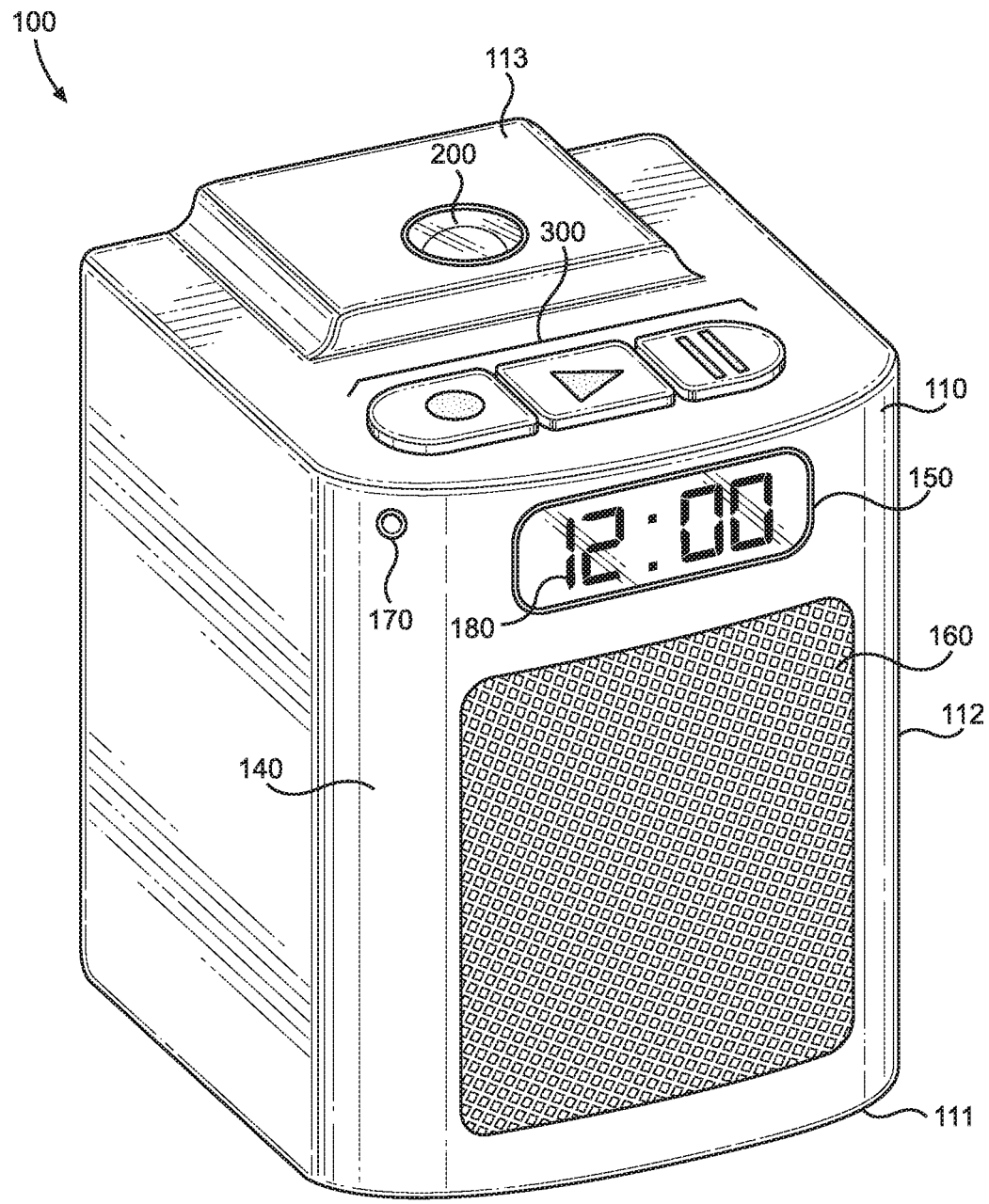
FIG. 1 shows a perspective view of an embodiment of the mental targeting system.

Reference is made herein to the attached drawings. Like reference numerals are used throughout the drawings to depict like or similar elements of the mental targeting system. For the purposes of presenting a brief and clear description of the present invention, a preferred embodiment will be discussed as used for the mental targeting system. The figures are intended for representative purposes only and should not be considered to be limiting in any respect.

In the interests of economy, the present disclosure refers to "a computer-readable medium," "a processor," and so on. However, this should not be read as limiting in any way as the present disclosure contemplates embodiments of the present invention utilizing "one or more computer-readable media," "one or more processors," and so on. Unless specifically limited to a single unit, "a" is intended to be equivalent to "one or more" throughout the present disclosure.

Referring now to FIG. 1, there is shown a perspective view of an embodiment of the mental targeting system. The mental targeting system 100 comprises a housing 110 that includes a base 111, at least one sidewall 112 extending from the base 111, and a top surface 113, together defining an interior volume. In one embodiment, the base 111 includes a non-slip surface disposed on an underside thereof, in order to provide greater stability to the mental targeting system 100 such that it will not slide off a surface. In one embodiment, the non-slip surface includes a coefficient of friction greater than one to prevent unwanted sliding. In one embodiment, the at least one sidewall 112 and the top surface 113 are a continuous piece of molded plastic to provide for a pleasing aesthetic of the device, as well as to provide structural integrity and lessen construction costs. It is contemplated by this disclosure that in some embodiments of the mental targeting system 100 the housing 110 is comprised of individual parts forming the base 111, the at least one sidewall 112, and the top surface 113. In other embodiments, such as in the shown embodiment, these individual parts may be molded together.

Figure 2:
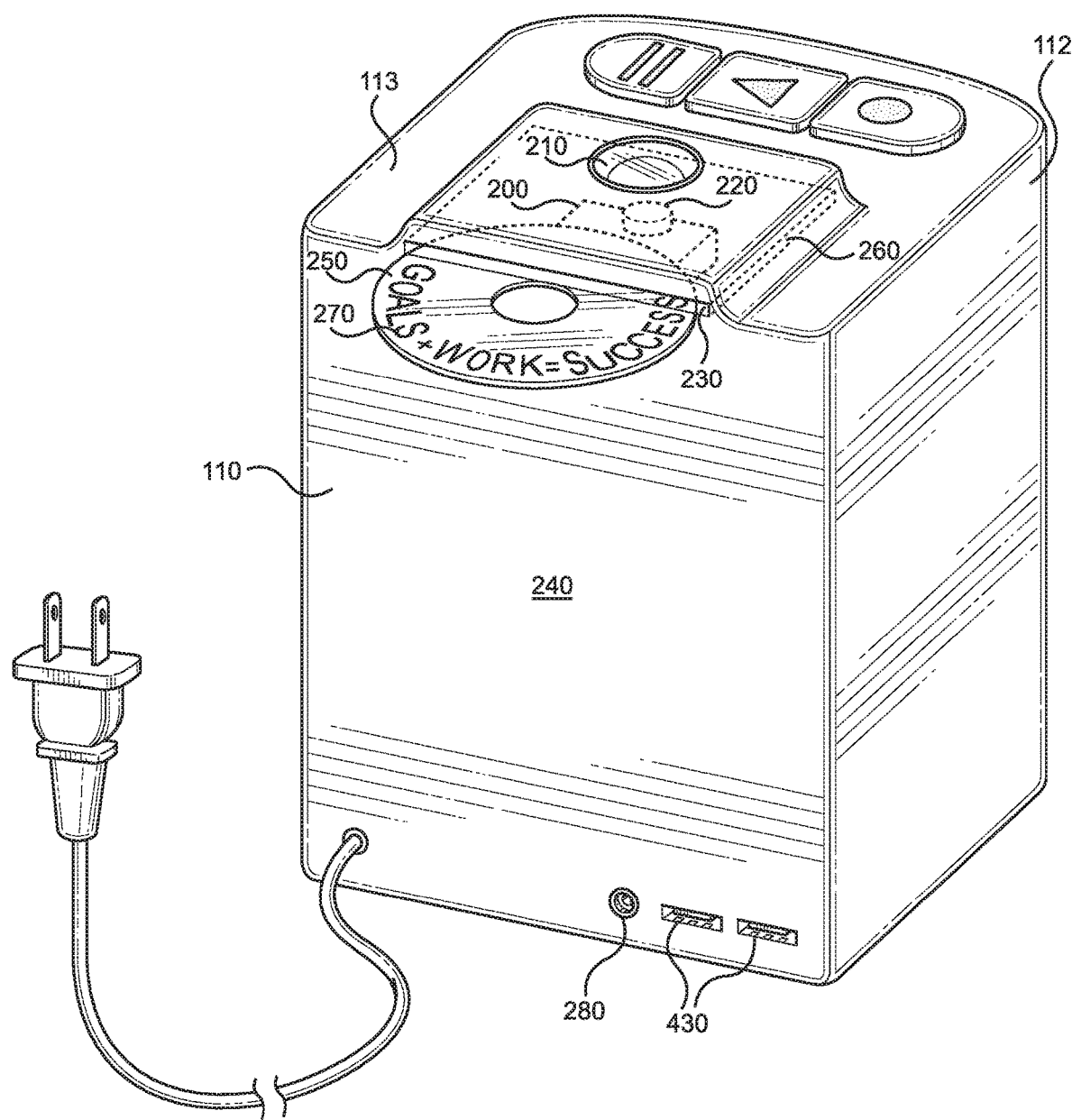
FIG. 2 shows a rear view of an embodiment of the mental targeting system.
Figure 4:
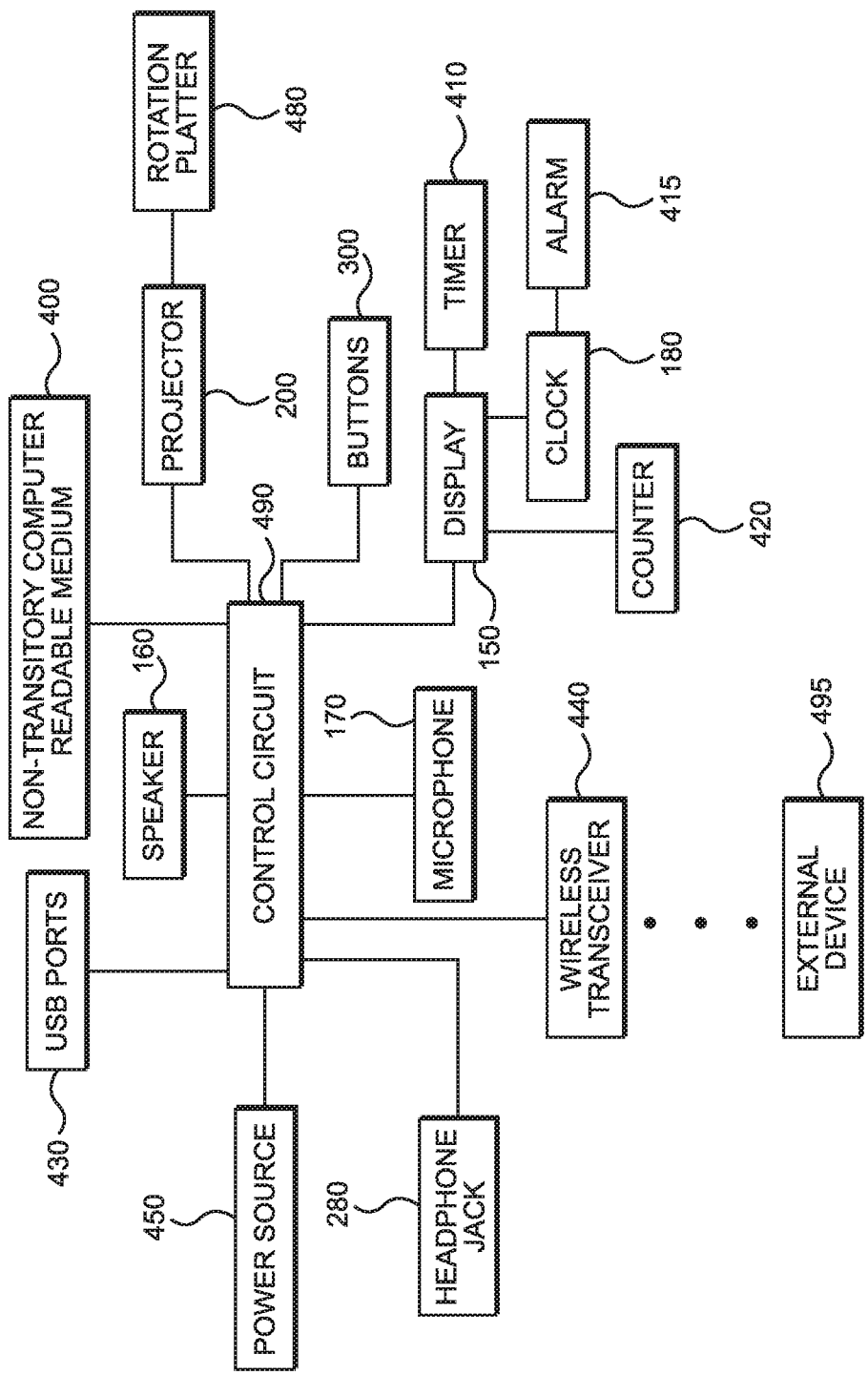
FIG. 4 shows a block diagram of the representative electronic components of the mental targeting system.

A control circuit shown in FIG. 4, 490), which is disposed in the interior volume, is in electrical communication with a speaker 160, a microphone 170, a projector 200, a plurality of buttons 300, and a non-transitory computer readable medium (as shown in FIG. 4, 400). In various other embodiments the control circuit is also in electrical communication with a display 150, a timer (as shown in FIG. 4, 410), a plurality of USB ports (as shown in FIG. 4, 430), a headphone jack (as shown in FIG. 2, 280), and a wireless transceiver (as shown in FIG. 4, 440). The control circuit is configured to selectively active and de-activate components that the control circuit is electrical communication with, based on user input and pre-defined parameters, as further detailed below.

The at least one sidewall 112 is configured to integrate a display 150. In the shown embodiment, the display 150 is integrated into a front surface 140 of the at least one sidewall 112. In one embodiment, the display 150 is operably connected to a clock 180. In such an embodiment, the display 150 is configured to show a time as determined by the clock 180. In a further embodiment, the display 150 can show the time based on a standard 24-hour clock format, or a standard 12-hour clock format. In one embodiment, the display 150 can show the time in a digital format. In another embodiment, the display 150 can show the time in an analogue format. In various embodiments, indicia can be shown on the display 150 that convey to a user various states of the mental targeting system 100 such as a low battery indicator, an AM/PM indicator, or an alarm indicator. In still further embodiments, the display 150 can be backlit, thereby providing a user with the ability to read the display 150 in a dark environment.

In one embodiment, the clock 180 is operably connected to an alarm (as shown in FIG. 4, 415), the alarm being in electrical communication with the control circuit. In such an embodiment, a user can pre-set a time at which various elements of the mental targeting device can be set to activate or deactivate, as further detailed below. In one embodiment, when the alarm is triggered, a message is played, and the projector is turned on. Such an alarm allows the user to maintain a daily habit of utilizing the mental targeting system at the same time each day. Such an alarm further allows the user to experience and utilize the mental targeting system as a method of waking up, and in such a manner, begin their day with the mental targeting experience being the first activity of a new day.

In one embodiment, the display 150 is in operable communication with a timer, the timer being in electrical communication with the control circuit. In such an embodiment the display 150 can show a time remaining as determined by the timer. A user can pre-set a time to be counted down by the timer, and the effects of the timer reaching the end of the pre-set time, as further detailed below Such a timer allows the user to customize the length and types of stimuli presented by the mental targeting system. For example, a user can set the timer for a 5-minute session, during which visual and audio stimuli are presented, as further detailed below. At the end of the 5-minute session, as determined by the timer, the stimuli can be turned off. In such a manner, the user can utilize the mental targeting system for a defined and customizable time.

In another embodiment, the display 150 is in operable communication with a counter (as shown in FIG. 4, 420), the counter being in electrical communication with the control circuit. In such an embodiment, the display 150 can show a count as determined by the counter as a 3-digit digital display. A count can be maintained as prescribed by certain conditions. In one embodiment, every time a user activates the mental targeting system 100 within 24-hours of a previous activation, wherein the timer provides a 24-hour countdown, the count can be incremented by one. In this manner the count can be a count of the number of consecutive days that a user activated and used the mental targeting system 100. Such a count can be utilized by the user as a score and said user can be promoted to attain a higher score by establishing consecutive day streaks. Such streaks help a user to get into the habit of using the mental targeting system 100 and the lessons as taught through such use.

The at least one sidewall 112 is configured to integrate a speaker 160. In the shown embodiment, the speaker 160 is integrated into a front surface 140 of the at least one sidewall 112. The speaker 160 is in operable communication with a non-transitory computer readable medium, which is in electrical communication with the control circuit. The non-transitory computer readable medium is configured to store a plurality of pre-recorded audio files. In one embodiment, the mental targeting system 100 contains three pre-recorded audio files which serve to introduce the user to the device and a suggested method of use. In another embodiment, a plurality of USB ports is in electrical communication with the control circuit, such that a user can plug an external device, such as a cellphone, mp3 player, or other source of audio files, into the USB ports, thereby enabling a user to utilize audio files from other, external sources. In one embodiment, these various pre-recorded audio files are selected via a plurality of buttons, as further detailed below. The speaker 160, in concert with the control circuit, plays the pre-recorded audio files such that a user can hear the audio via the speaker 160.

In one embodiment, a headphone jack is disposed in the at least one sidewall 112. The headphone jack is configured to receive a complementary audio cable, and where such a cable is connected, the mental targeting system 100 plays the audio into the connected device, such as a set of headphones or earphones. In one embodiment, the speaker 160 is in operable communication with the headphone jack. In a further embodiment, insertion of a headphone cable into the headphone jack disables the speaker 160 and plays the audio only through the connected headphones. In another embodiment, a set of wireless headphones is in wireless communication with the wireless transceiver (as shown in FIG. 4, 440). In such an embodiment, the audio is wirelessly transmitted to the set of wireless headphones such that a user can hear the audio through the set of wireless headphones. In a further embodiment, connection of the set of wireless headphones to the wireless transceiver disables the speaker 160 and plays the audio only through the connected set of wireless headphones.

The at least one sidewall 112 is configured to integrate a microphone 170. In the shown embodiment, the microphone 170 is integrated into a front surface 140 of the at least one sidewall 112. The microphone 170 is in operable communication with the non-transitory computer readable medium. The microphone 170 is utilized by a user to provide audio input that is stored as a pre-recorded audio file in the non-transitory computer readable medium. In one embodiment, the non-transitory computer readable medium can store up to five separate user-provided audio inputs. In such a manner, a user customizes and personalizes the audio played via the mental targeting system 100.

Referring now to FIG. 2, there is shown a rear view of an embodiment of the mental targeting system. A projector 200 disposed in the interior volume is configured to project light through a projection lens 210. The projector 200 includes a light source 220, such as a lightbulb. The projection lens 210 is integrated into the top surface 113 of the housing 110. A slot 230 is disposed on a rear surface 240 of the at least one sidewall 112 and is dimensioned to receive a disc 250.

The disc 250 is comprised of a translucent material, with opaque indicia 270 disposed thereon. In the shown embodiment the indicia 270 are the characters: GOALS+WORK=SUCCESS. In one embodiment, the disc 250 is configured to allow light to pass through the translucent portions thereof, while blocking light from passing through the opaque portions thereof. In other embodiments, various opacities and colors are utilized in the indicia 270 to further add color and depth to a projected image resulting from the transmission of light through the disc 250. In one embodiment, the disc 250 can be fully customized such that a user can craft their own specific indicia and messages that are projected. A channel 260 in the interior volume is defined by an area between the slot 230 and a position above the light source 220 that is also below the projection lens 210. In such a configuration a user can insert a disc 250 into the channel 260 via the slot 230.

Figure 3:
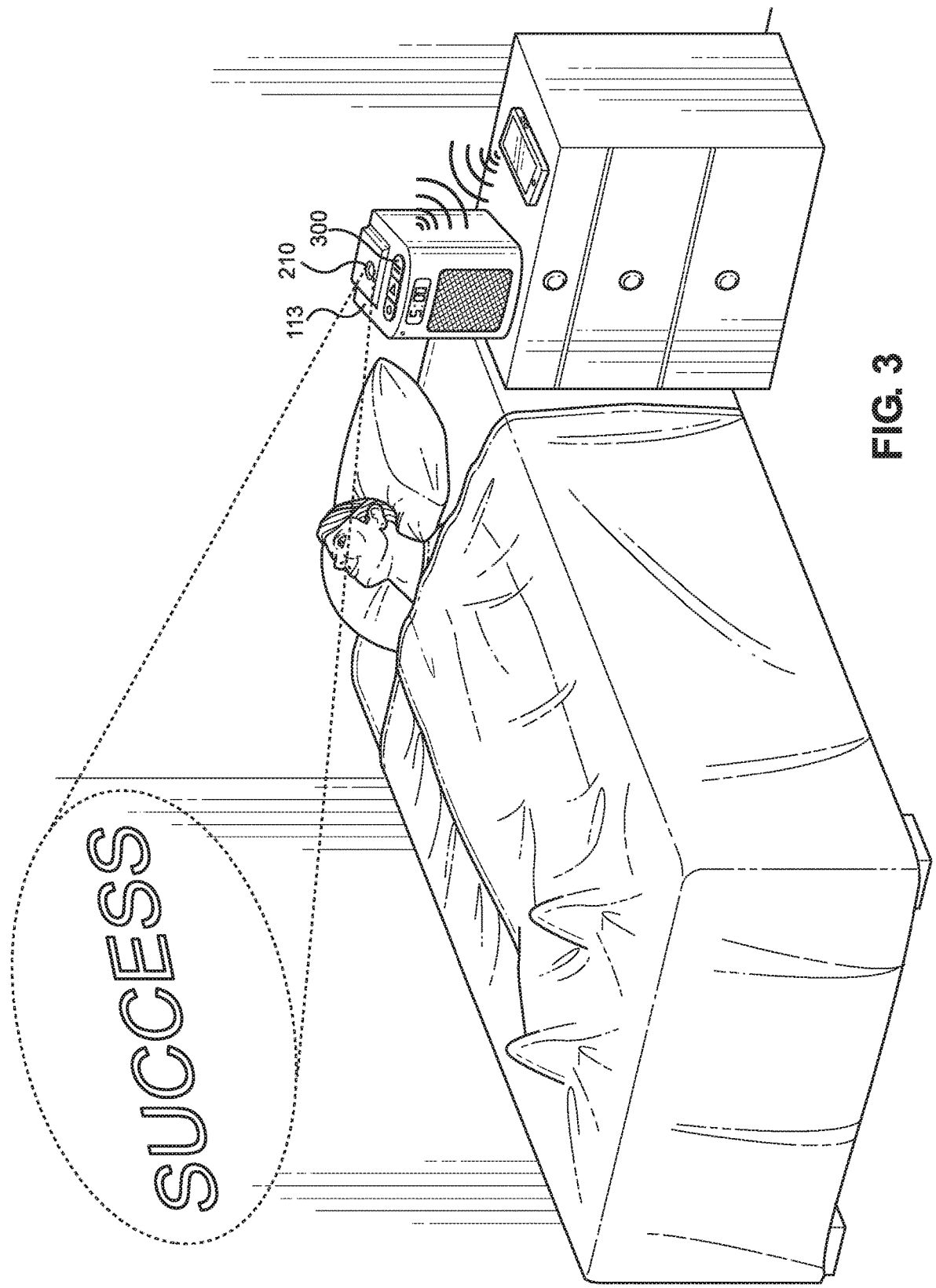
FIG. 3 shows a perspective view of an embodiment of the mental targeting system, in use.

Referring now to FIG. 3, there is shown a perspective view of an embodiment of the mental targeting system, in use. Full insertion of the disc positions a portion of the disc directly below, and parallel with, the projection lens 210. In such a manner, a given portion of the disc is positioned between the illumination source and the projection lens. For example, in the shown embodiment, that portion of the disc with the indicia "SUCCESS" is positioned between the illumination source and the projection lens, thereby projecting the word "SUCCESS" onto the ceiling. The projector also includes a rotation platter (as shown in FIG. 4, 480) which rotates the disc. Through rotation of the disc via the rotation platter, a new portion of the disc is positioned between the illumination source and the projection lens. In such a manner each segment of the disc is rotated into position and individual indicia are projected via the mental targeting system. For example, the indicia "GOALS" are initially displayed. As the disc is rotated into position between the illumination source and the projection lens 210 the indicia "+", "WORK", "=", and "SUCCESS" are in turn projected onto the ceiling. In such a manner, the user is presented with the visual stimuli: GOALS+WORK=SUCCESS. As the rotation continues the first indicia "GOALS" is projected after "SUCCESS", and in such a manner the message repeats.

A plurality of buttons 300 is disposed on the at least one sidewall. The plurality of buttons 300 provide a user with a way to input commands to the control circuit. In one embodiment, the plurality of buttons 300 include buttons for play, pause, and record and are disposed on the top surface 113. In such an embodiment activation of the play button causes the control circuit to activate the illumination source, thereby projecting indicia via the projector, and to activate the speaker to play a pre-selected audio file. The pause button temporarily stops such activation until the play button is activated again. The record button allows a user to provide audio input which is recorded, via the microphone, into a non-transitory computer readable medium. In such a manner, a user creates an audio file that is available to be played back. In other embodiments, the plurality of buttons provide the user with the ability to select whether the speaker and projector are activated at the same time, which audio file to file, which non-transitory computer readable medium to record audio to, how long to set a timer, a way to set the clock, and the selection of an external device connected via a USB port. Input regarding other interactions between the various elements of the present disclosure are also contemplated by this disclosure, and it is considered that the plurality of buttons provides the user with a variety of input modalities to the control circuit, and thereby, the function of the independent elements of the present invention.

Referring now to FIG. 4, there is shown a block diagram of the representative electronic components of the mental targeting system. In various embodiments, the control circuit 490 is in electrical communication with a power source 450, a headphone jack 280, a plurality of USB ports 430, a speaker 160, a microphone 170, a plurality of non-transitory computer readable mediums 400, a projector 200, a plurality of buttons 300, a display 150, and a wireless transceiver 440. The display 150 is in operable communication with a timer 410, a counter 420, and a clock 180. The projector 200 is in operable communication with a rotation platter 480.

The wireless transceiver 440 is in wireless communication with an external device 495 such as a cellphone, tablet, mp3 player, or similar device capable of providing input and/or audio files. In one embodiment the wireless transceiver 400 is in wireless communication with a set of wireless headphones, such that audio is capable of being transmitted via the wireless transceiver to the set of wireless headphones. In one embodiment, the mental targeting system is in wireless communication with an application installed on a computing platform such as a cellphone, tablet, or computer. In such an embodiment the application can provide a way for a user to input commands to the control circuit 490 and to receive commands from the control circuit 490. Further, in such an embodiment, the application also tracks and records the user's usage of the mental targeting system.

In use, a user positions the mental targeting system in a desired location in a room. The user then activates the mental targeting system via the plurality of buttons 300 and listens to pre-recorded audio while corresponding visual stimuli are presented. In one embodiment, a series of pre-recorded introductory messages and corresponding discs 350 guide the user through the functions of the mental targeting system and explain how the user can provide input to customize and personalize their experience. The user can create their own transparent discs 250 to customize and personalize the visual stimuli, and the user can record audio via the microphone 170 into the non-transitory computer readable medium 400 to customize and personalize the audio stimuli. USB ports 430 and a wireless transceiver 440 are utilized as alternate sources of audio stimuli. The speaker 160 and headphone jack 280 provide the user with a choice of how the audio stimuli is presented to the user.

The alarm 415 and the clock 180 are utilized as a way for the user to select the time at which such stimulation can be pre-set to commence. The timer 410 is utilized to select the length of time that the stimulation is presented. The counter 420 is utilized to keep track of when the user activated the mental targeting system. The plurality of buttons 300 and the wirelessly connected external device 495 are utilized by the user to provide input to the control circuit 490, and in such a manner control the various elements of the mental targeting device, as detailed above, to create completely customizable audio and visual stimuli, and in such a way a personalized experience to the user. Through utilization of the mental targeting device, via the audio and visual stimuli, the user is presented with stimuli that aids the user in setting and achieving goals by guided meditation and contemplation.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A mental targeting system, comprising:
    a housing including a base, at least one sidewall extending from the base, and a top surface, defining an interior volume;
    a control circuit disposed in the interior volume;
    wherein the control circuit is in electrical communication with a speaker, a microphone, a projector, a plurality of buttons, and a non-transitory computer readable medium;
    the speaker disposed in the at least one sidewall;
    wherein the speaker is configured to play a plurality of sounds stored in the non-transitory computer readable medium;
    the projector including a projection lens disposed on the top surface of the housing, the projector configured to project light through the projection lens;
    a slot disposed in the at least one sidewall, the slot configured to receive a disc therein;
    wherein full insertion of the disc into the slot positions a portion of the disc directly below the projection lens.

2. The mental targeting system of claim 1, further comprising a backlit display.

3. The mental targeting system of claim 2, wherein the backlit display further comprises a clock.

4. The mental targeting system of claim 1, wherein the projector is configured to rotate the disc.

5. The mental targeting system of claim 1, wherein the disc is transparent.

6. The mental targeting system of claim 5, wherein the disc further includes opaque indicia.

7. The mental targeting system of claim 1, further comprising a headphone jack.

8. The mental targeting system of claim 7, wherein the speaker is in operable communication with the headphone jack.

9. The mental targeting system of claim 8, wherein insertion of a headphone cable into the headphone jack disables the speaker and plays the plurality of sounds through one or more headphones connected to the headphone cable.

10. The mental targeting system of claim 1, further comprising a display in operable communication with the control circuit.

11. The mental targeting system of claim 10, wherein the display is disposed on a front surface of the at least one sidewall.

12. The mental targeting system of claim 1, further comprising a timer.

13. The mental targeting system of claim 12, wherein the timer is in operable communication with the projector and speaker;
    wherein the timer is configured to selectively activate and de-activate the projector after a first pre-determined amount of time has elapsed;
    wherein the timer is configured to selectively activate and de-activate the speaker after a second pre-determined amount of time has elapsed.

14. The mental targeting system of claim 1, further comprising a plurality of USB ports.

15. The mental targeting system of claim 1, further comprising a wireless transceiver in operable communication with the control circuit.

16. The mental targeting system of claim 1, wherein the plurality of buttons includes a play button, a pause button, and a record button.

* * * * *